United States Patent
Tjong Joe Wai

(10) Patent No.: US 7,900,634 B2
(45) Date of Patent: Mar. 8, 2011

(54) BRONCHUS BLOCKER AND ARTIFICIAL RESPIRATION SYSTEM

(75) Inventor: Peter Tjong Joe Wai, Amsterdam (NL)

(73) Assignee: EZ-Blocker B.V., Rotterdam (NL)

( * ) Notice: Subject to any disclaimer, the term of this patent is extended or adjusted under 35 U.S.C. 154(b) by 984 days.

(21) Appl. No.: 11/579,676

(22) PCT Filed: May 13, 2005

(86) PCT No.: PCT/NL2005/000369
§ 371 (c)(1),
(2), (4) Date: Dec. 7, 2006

(87) PCT Pub. No.: WO2005/110247
PCT Pub. Date: Nov. 24, 2005

(65) Prior Publication Data
US 2008/0190434 A1 Aug. 14, 2008

(30) Foreign Application Priority Data
May 13, 2004 (NL) .................................. 1026190

(51) Int. Cl.
*A61M 11/00* (2006.01)
(52) U.S. Cl. .................................................. 128/207.15
(58) Field of Classification Search ............. 128/207.15, 128/207.16
See application file for complete search history.

(56) References Cited

U.S. PATENT DOCUMENTS

| | | | | | |
|---|---|---|---|---|---|
| 4,453,545 | A | * | 6/1984 | Inoue | 128/207.15 |
| 4,840,172 | A | * | 6/1989 | Augustine et al. | 128/207.14 |
| 5,588,424 | A | * | 12/1996 | Insler et al. | 128/207.15 |
| 5,720,735 | A | * | 2/1998 | Dorros | 604/284 |
| 7,013,890 | B2 | * | 3/2006 | Wakabayashi | 128/200.26 |
| 2003/0154988 | A1 | | 8/2003 | DeVore et al. | |
| 2004/0060563 | A1 | | 4/2004 | Rapacki et al. | |

FOREIGN PATENT DOCUMENTS
WO WO 01/02042 A1 1/2001

\* cited by examiner

*Primary Examiner* — Steven O Douglas
(74) *Attorney, Agent, or Firm* — Hoffmann & Baron, LLP

(57) ABSTRACT

The bronchus blocker according to the invention comprises an insertion rod and a blocking means. The blocking means is provided near one end of the insertion rod in order to be inserted by means thereof into a bronchus. The bronchus blocker furthermore comprises a support, for supporting the bronchus blocker on a bronchial branching, such as the carina. By supporting the bronchus blocker on a bronchial branching using its support, the inflated balloon only has to seal the bronchus and does not also have to keep the bronchus blocker in its position at the same time. As a result, the risk of the bronchus blocker slipping out of its position is much smaller than with the prior art.

12 Claims, 4 Drawing Sheets

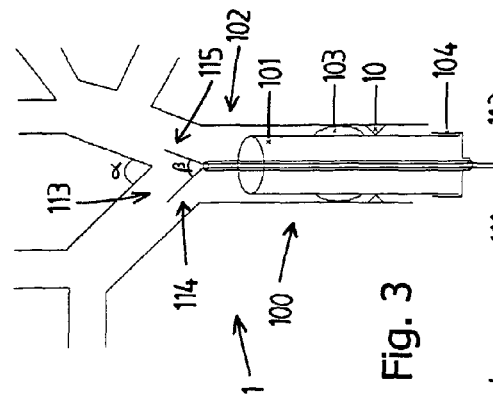
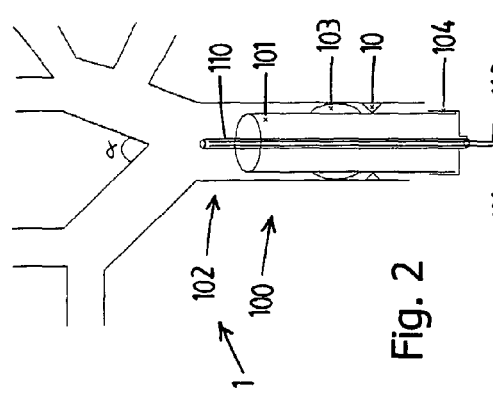
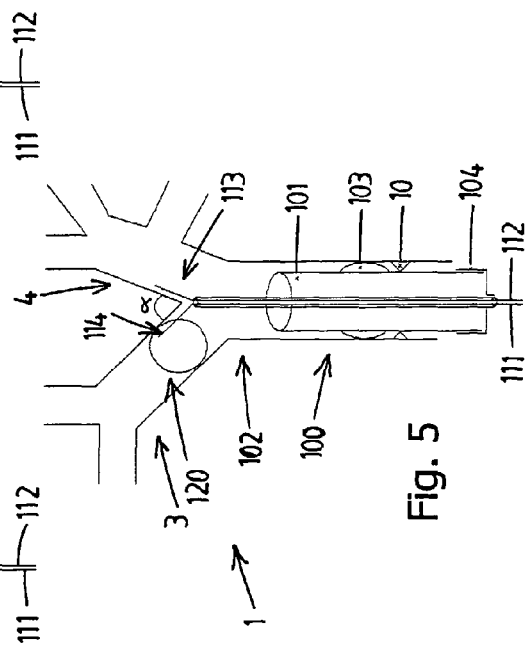
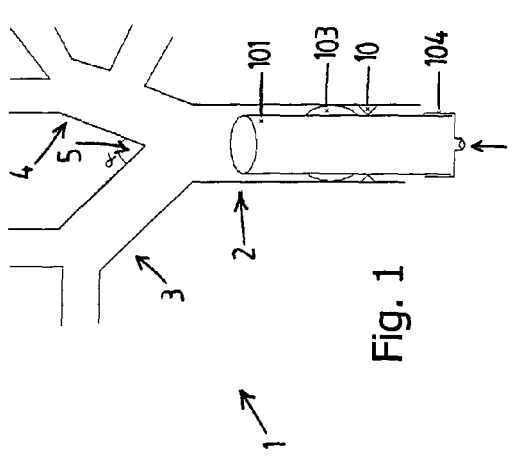

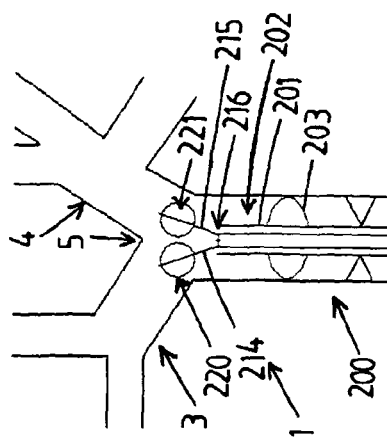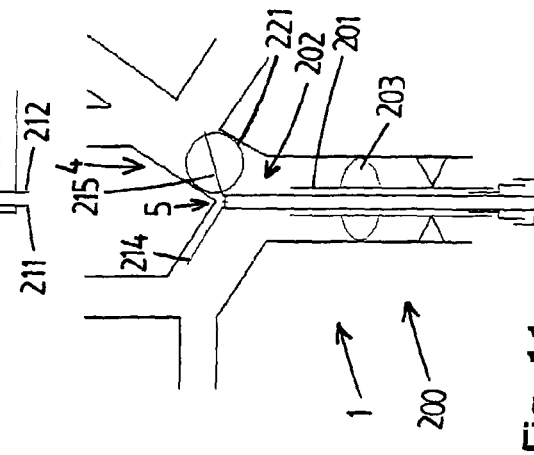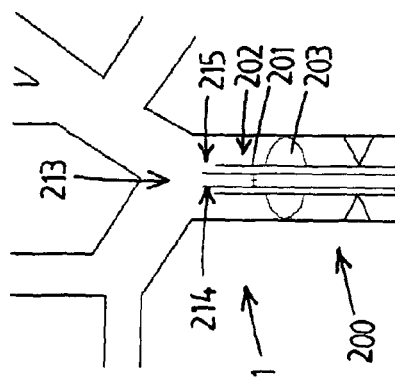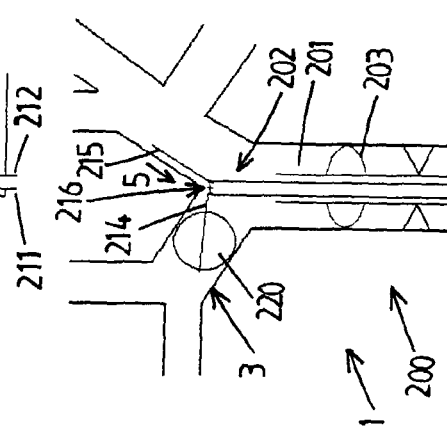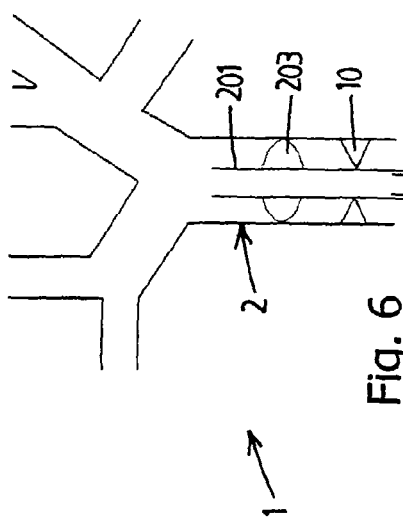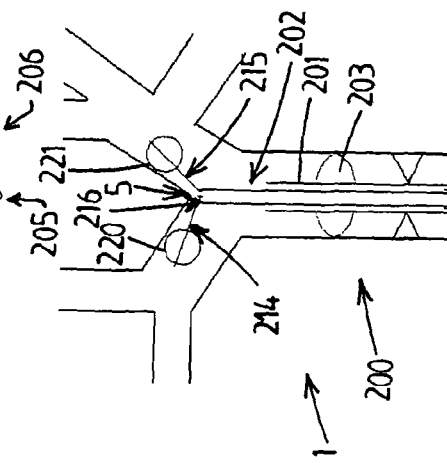

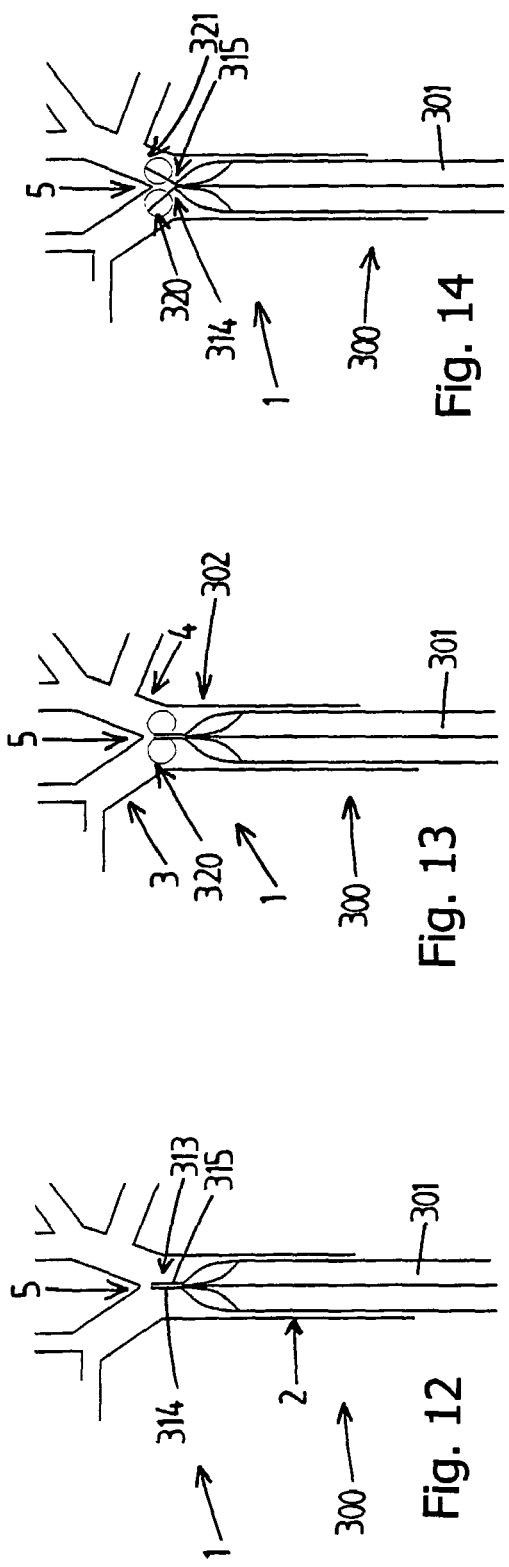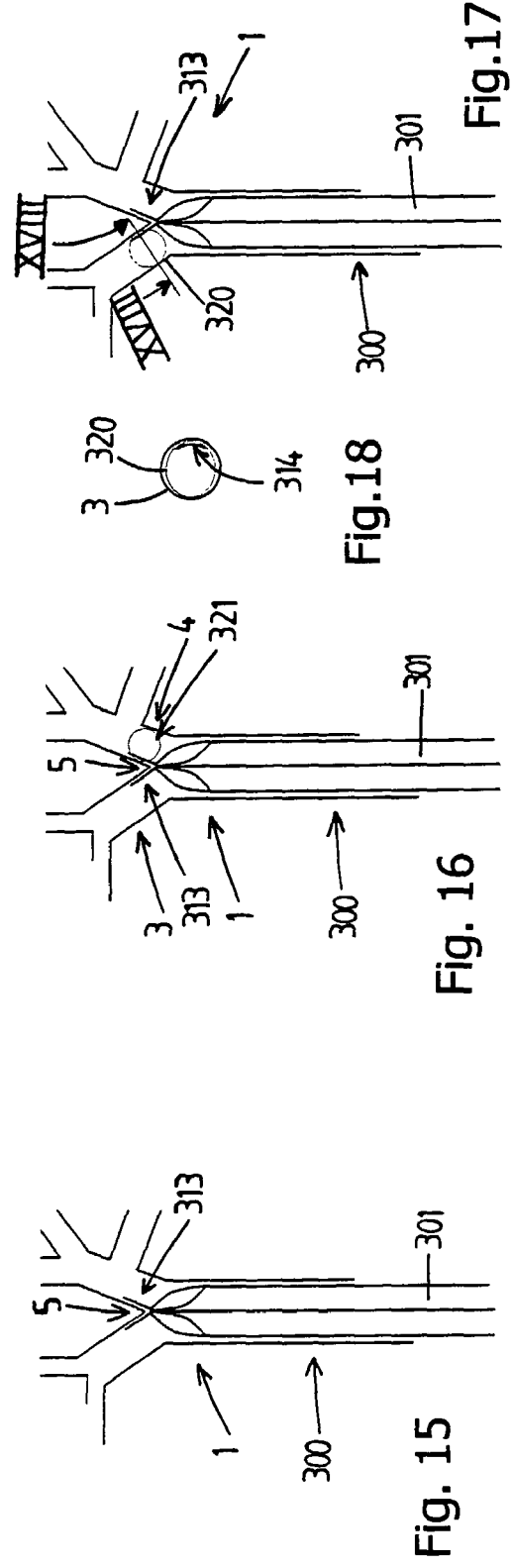

BRONCHUS BLOCKER AND ARTIFICIAL RESPIRATION SYSTEM

CROSS-REFERENCE TO RELATED APPLICATIONS

This application is the National Stage of International Application No. PCT/NL2005/000369, filed May 13, 2005, which claims the benefit of Netherlands Application No. NL 1026190, filed May 13, 2004, the contents of which are incorporated by reference herein.

FIELD OF THE INVENTION

The invention relates to a bronchus blocker according to the preamble of claim 1. A bronchus blocker of this type is used to seal a bronchus air-tight, for example in order to be able to selectively apply artificial respiration to a part of the lungs.

BACKGROUND OF THE INVENTION

A known bronchus blocker includes a thin, slightly flexible tube to the end of which a balloon is attached. This balloon is inflatable through a lumen of the tube. The end of the tube to which the balloon is attached is at an angle with respect to the remainder of the tube.

In use, a respiration tube is inserted into the trachea of a patient. The bronchus blocker is inserted through or along this respiration tube. In addition, an endoscope is inserted through the respiration tube which is used to detect if the bronchus blocker has been inserted sufficiently far so that it is just in front of the branching of the trachea into bronchi near the carina. The bronchus blocker is then turned about its axis to such a degree, that the end points in the direction of the bronchus to be sealed off. Thereafter, the bronchus blocker is inserted into this bronchus. Finally, the balloon is inflated to such a degree that the bronchus is sealed air-tight.

A disadvantage of this known bronchus blocker is that the inflated balloon slips out of the bronchus relatively easily or is pushed too far into the latter. If a patient moves his/her head relative to the neck, the tract from the patient's mouth to the carina becomes longer or shorter. If the flexible tube is partly or completely carried along with such a movement of the head, or tension or pressure is inadvertently exerted on the tube in any other way, this will result in a corresponding force on the balloon. As the balloon should not be held in the bronchus too tightly or with too much friction in order to prevent damaging the latter, such a movement will quickly result in an undesired displacement of the balloon. The result of this is that the artificial respiration air is erroneously also being blown into a part of the lungs which is being operated on or amputated, which may even cause blood to be blown out of the patient which may soil staff who are surrounding the patient. The balloon then has to be brought into position again before artificial respiration can be resumed. To this end, the balloon is deflated and an endoscope is inserted again in order to be able to position the balloon, following which the balloon can be inflated again.

SUMMARY OF THE INVENTION

It is an object of the present invention to provide a bronchus blocker which at least partially overcomes these drawbacks or to provide a usable alternative.

In particular, it is an object of the invention to reduce the risk of the bronchus blocker inadvertently coming out of its active position.

DETAILED DESCRIPTION OF PREFERRED EMBODIMENTS

According to the invention, this object is achieved by a bronchus blocker according to claim 1. The bronchus blocker comprises an insertion rod and a blocking means for sealing a bronchus. The blocking means is provided near one end of the insertion rod in order to be inserted by means thereof into a bronchus. The bronchus blocker furthermore comprises a support for supporting the bronchus blocker on a bronchial branching, such as a carina.

By supporting the bronchus blocker on a bronchial branching using its support, the blocking means, for example an inflated balloon, only has to seal the bronchus and does not also have to keep the bronchus blocker in its position at the same time. As a result, the risk of the bronchus blocker slipping out of its position is much smaller than with the prior art.

The bronchus blocker according to the invention further has the advantage that it can be inserted without using an endoscope. The bronchus blocker can be inserted up to the point where its support touches the bronchial branching. As soon as this is detected, the position of the blocking means relative to the bronchial branching is known, so that no endoscope is required for further activating the blocking means.

In particular, the support is fitted on the insertion rod so as to be movable, in order to occupy either a supporting position or an insertion position. In the insertion position, the support protrudes as little as possible relative to the insertion rod so that it can be inserted without getting caught in, for example, the vocal cords. After it has passed the vocal cords, or at least before it reaches the bronchial branching, the support is moved into the supporting position.

More particularly, the support is rotatable with respect to the insertion rod. As a result, the support takes up little space in a screwed-in position and can create a maximum support area in a screwed-out position.

In one variant, the support can be displaced laterally with respect to the insertion rod. This makes it possible for the insertion position of the support to be in or near the insertion rod. By moving the support laterally with respect to the insertion rod, it comes out of its insertion position and can move laterally by translation and/or rotation in order to create a supporting surface in this way.

In one embodiment, the support comprises two support parts which are each intended for support on either side of the bronchial branching. Dividing the support into two support parts of this type increases the stability of support on the bronchial branching and also ensures that the pressure from the support on the branching is distributed over a larger surface area. Support parts of this type may be fixedly connected to one another. In particular, the respective support parts may be movable individually with respect to the insertion rod, in order to achieve effective insertion and support positions in a simple manner.

In one specific form, at least one support part is expandable. This makes it possible for the support part to be enlarged after it has passed the vocal cords, as a result of which it can be introduced in a simple manner into a bronchus and the forces which the respective support part exerts on the bronchial branching or wall part of a bronchus are distributed over a larger surface area.

The expandable support part is in particular a balloon which is inflatable via a lumen in the insertion rod. This is a form of a support part which is very simple and easy to operate. In addition, a balloon-shaped support part of this type may also serve as a blocking means by inflating it further after it has been inserted.

The invention also relates to a system comprising a bronchus blocker and a respiration tube according to claim 9. The respiration tube comprises at least one first lumen. The bronchus blocker is inserted into a trachea via the respiration tube. This can be effected either by inserting the bronchus blocker together with the respiration tube or by inserting the bronchus blocker through a lumen of the respiration tube or along the respiration tube. The respiration tube can thus facilitate the insertion of the bronchus blocker.

An artificial respiration system of this type makes it possible, if desired, to apply artificial respiration to one part of the lungs, with the other part being sealed by the bronchus blocker. It is not necessary to insert a respiration tube into a bronchus in order to achieve this. This is very advantageous since the dimensions of a respiration tube which is to be inserted into a bronchus are very critical. If the tube is too narrow, not enough artificial respiration air is supplied and discharged, whereas if the tube is too wide, it may not fit the respective bronchus or it may—if the fit is too tight—irritate or damage the latter.

In particular, the artificial respiration system furthermore comprises a compensating device which connects the bronchus blocker and the respiration tube with one another so that they are movable in the longitudinal direction in such a manner that the bronchus blocker can remain supported against the bronchial branching while the respiration tube moves relative thereto. This prevents the bronchus blocker from being pulled out of the bronchus or from exerting excessive pressure on the bronchial branching.

More particularly, the compensating device comprises spring means. These enable the compensating device to press the support against the bronchial branching using a certain spring force.

In one embodiment, the respiration tube functions as the insertion rod. By integrating the functions of the respiration tube and insertion rod in one tube, a compact and relatively inexpensive artificial respiration system is realized.

Further preferred embodiments of the invention are defined in the subclaims.

The invention furthermore relates to the use of a bronchus blocker for sealing off a bronchus of a respiratory system according to claim 15.

BRIEF DESCRIPTION OF THE DRAWINGS

One embodiment of the invention will be explained in more detail with reference to the accompanying drawing, in which:

FIGS. 1-5 show the operation of a first embodiment of the invention in successive stages;

FIGS. 6-11 show the operation of a second embodiment of the invention in successive stages;

FIGS. 12-17 show the operation of a third embodiment of the invention in successive stages;

FIG. 18 shows a section along line XVIII-XVIII in FIG. 17;

Figure 19:
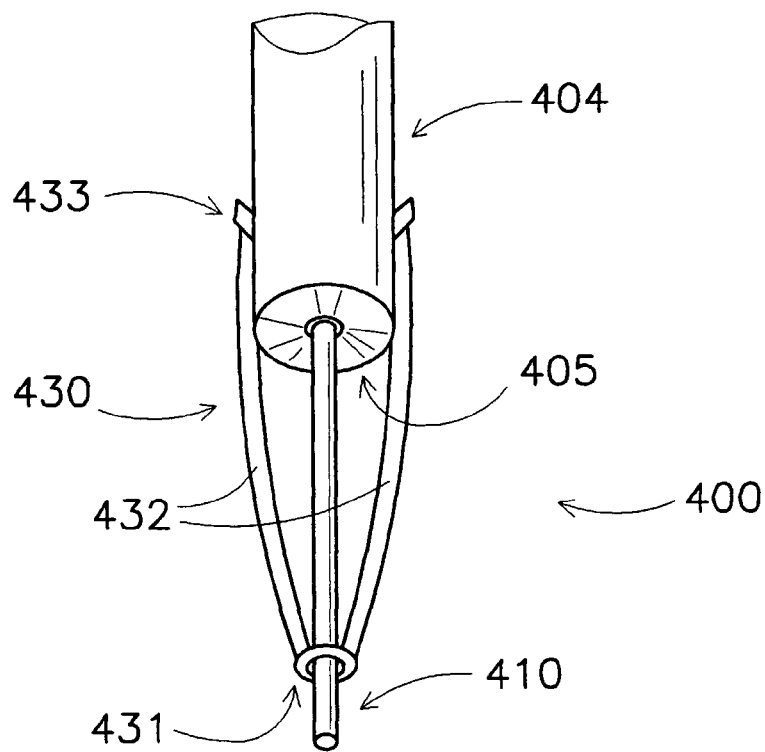
FIG. 19 shows a first embodiment of a compensating device.

In all figures, a respiratory system is denoted in its entirety by reference numeral 1. The respiratory system 1 comprises a trachea 2, a left main bronchus 3, a right main bronchus 4 and a carina 5. The left 3 and right 4 main bronchi are at an angle α with respect to one another, with α in practice being approximately 60°. From the left and right bronchi 3, 4, various bronchi lead to the left upper and lower lobes, and right upper, middle and lower lobes of the lungs (not shown in any more detail). The vocal cords 10 are located at the start of the trachea 2.

An artificial respiration system 100, according to a first embodiment of the invention, comprises a respiration tube or endotracheal tube 101 and a bronchus blocker 102. An expandable sealing means, known as a cuff 103, is provided around the circumference of the respiration tube 101. The cuff 103 can be inflated by means of a small tube or hose (not shown) which is optionally run through the respiration tube 101 or is recessed therein. The components of the artificial respiration system 100, at least those parts which are inside the respiratory system 1 during use, are preferably made of a somewhat flexible and soft, yet air-tight and sterilizable material, such as soft plastics, silicone, latex or India rubber.

At the end of the artificial respiration tube 101 which is located outside the trachea 2, an airway adapter or swivel connector 104 is provided. The swivel connector 104 comprises an opening (not shown) for supplying and discharging artificial respiration air, as well as an airtight seal or diaphragm 105, through which a tube or rod can be inserted in a sealing manner.

The bronchus blocker 102 comprises a first hollow insertion rod or tube-shaped holder 110. A second and third hollow insertion rod are slidably incorporated in the tube-shaped holder 110, and are designed as insertion tubes or insertion catheters 111 and 112. A support 113 is arranged at the ends of the insertion tubes 111 and 112. The support 113 comprises a first and a second support part 114 and 115, which are provided so as to be resiliently pivotable on the respective insertion tubes 111 and 112. In their released state, the support parts 114 and 115 are at an angle β of approximately 60° with one another, i.e. an angle β which is approximately equal to the angle between the left and the right main bronchus 3, 4.

On the first support part 114, a first blocking means is provided in the form of a bronchus balloon 120, also known as a bronchus blocker. Likewise, on the second support part a bronchus balloon (not shown) may be provided. The inside of the bronchus balloon 120 is in open communication with the lumen of the insertion tube 111 via a lumen of the support part 114. By means of these lumens, the bronchus balloon can be inflated and deflated.

In use, a respiration tube 101 is first inserted in the trachea 2. After this has been positioned, the cuff 103 is inflated, as a result of which the lungs can only be provided with air via the interior of the respiration tube 101. Subsequently, the tube-shaped holder 110 with insertion tubes 111 and 112 can be inserted through the airtight diaphragm 105 of the swivel connector 104 (FIG. 2).

As soon as the end of the tube-shaped holder 110 protrudes sufficiently from the respiration tube 101 and is in the vicinity of the carina 5, the insertion tubes 111 and 112 are pushed through the tube-shaped holder 110 in their longitudinal direction. As soon as the support parts 114 and 115 protrude completely from the tube-shaped holder 110, they will swivel out into their predetermined orientations due to their resilience (FIG. 3).

Thereafter, the insertion tubes 111 and 112 can be inserted further, optionally together with the tube-shaped holder 110, as shown in FIG. 4, so that the support 113 comes to rest against the carina 5. After this position has been reached, the bronchus balloon 120 is inflated via the lumens of insertion tube 111 and support part 114 which results in an effective airtight sealing of the left bronchus 3 (FIG. 5). As a result, artificial respiration air which is supplied to and discharged from the respiration tube 101 via the swivel connector 104 through an opening (not shown), will only be able to enter and exit the right bronchus 4.

A continuous slight pressure may be exerted on the bronchus blocker 102 which is absorbed via the support 113 on the carina 5, without this causing the bronchus balloon 120 to be pressed too far into the bronchus 3. This continuous slight pressure prevents the bronchus balloon 120 from inadvertently being pulled out of the bronchus 3 which makes it possible to carry out an operation or amputation on the left lung in a safe manner. Obviously, it is possible to inflate a second bronchus balloon (not shown) inside the right bronchus in a similar manner, as a result of which an operation may be performed on the right lung.

A second embodiment 200 of an artificial respiration system according to the invention comprises a respiration tube 201 and a bronchus blocker 202. A cuff 203 is provided around the circumference of the respiration tube 201, with a similar action to that described with reference to FIGS. 1-5.

At the end of the respiration tube 201, a swivel connector 204 is provided, having a diaphragm 205 and an air supply and discharge 206. Instead of one diaphragm 205, a plurality of diaphragms may be provided.

A first and second hollow insertion tube 211, 212 protrude from the one diaphragm 205 or the plurality of diaphragms. The hollow rods 211 and 212 are designed as relatively flexible tubes, which form a support 213 at their first end. The support 213 comprises support parts 214 and 215 which are formed by the ends of the respective flexible tubes 211 and 212. The flexible tubes 211 and 212 are connected to one another by means of a bridge piece 216 in order to form the support 213. This bridge piece 216 may be a direct connection at the location of the flexible tubes 211 and 212 by means of gluing, bonding or by forming the tubes 211 and 212 as one composite tube and subsequently splitting it to form the support 213. The bridge piece 216 may also be a separate element as a result of which the flexible tubes 211 and 212 may be kept apart locally. In this case, the bridge piece 216 is made from a relatively soft material, such as soft plastic, silicone, latex or India rubber.

The support parts 214 and 215 comprise bronchus balloons 220 and 221, respectively. The bronchus balloons 220 and 221 play a part both for the support 213, and possibly also in blocking the bronchi 3, 4.

In use, the respiration tube 201 is inserted first and connected in an airtight manner to the trachea 2 using the cuff 203 (FIG. 6). The bronchus blocker 202 is inserted via the diaphragm 205 or the plurality of diaphragms (FIG. 7).

As soon as the support parts 214 and 215 protrude from the respiration tube 201, the bronchus balloons 220 and 221 are inflated to a certain degree, for example half-full. This causes the support parts 214 and 215 to be pushed apart (FIG. 8). The bronchus blocker 202 may now be pushed further into the trachea 2, until the bronchus balloons 220 and 221 reach the carina 5 and each slide into a separate bronchus 3, 4 there. The bronchus blocker 202 is pushed until the support parts 214, 215 and optionally the connecting bridge 216 are supported against the carina 5 (FIG. 9).

Subsequently, a balloon, for example the bronchus balloon 221, may be deflated and the other balloon, for example bronchus balloon 220 may be further inflated until the latter seals off the respective bronchus 3 (FIG. 10). Obviously, in a similar manner, the bronchus balloon 220 may also be deflated and bronchus balloon 221 further inflated in order to seal off bronchus 4.

By exerting a slight pressure on the bronchus blocker 202, the latter can be held in position against the carina 5 without the bronchus balloon 220, or 221, slipping too far into the respective bronchus 3, 4 or, on the contrary, is pulled out of the latter. It is subsequently possible to perform an operation on the lungs in the manner described above.

A third embodiment of the invention is shown in FIGS. 12-18. An artificial respiration system 300 comprises a respiration tube 301 and a bronchus blocker 302. The insertion rod of the bronchus blocker 302 is in this embodiment formed by the respiration tube 301. The respiration tube 301 is of the kind known as double-lumen type and thus comprises two separate lumens for giving artificial respiration to the left and/or right half of the lungs. A cuff (not shown here) may be provided around the respiration tube 301.

A support 313 is provided on a first end of the respiration tube 301 and substantially near its centre line, which support 313 comprises the support parts 314 and 315. The support parts 314 and 315 have a round diameter (see FIG. 18), rest against each other in the at-rest position and essentially extend in the longitudinal direction of the respiration tube 301.

Bronchus balloons 320 and 321 are provided on the support parts 314 and 315. The bronchus balloons 320 and 321 extend around the respective support parts 314 and 315 (FIG. 18). Two separate lumens (not shown) extend through the respiration tube 301 and the support parts 314 and 315, through which the respective bronchus balloons 320 and 321 can be inflated and deflated.

In use, the respiration tube 301 is inserted into the trachea 2 until the support parts 314 and 315 are in the vicinity of the carina 5 (FIG. 12). Subsequently, the bronchus balloons 320 and 321 are inflated to a certain degree (FIG. 13) and the respiration tube 301 is inserted further until the support parts 314 and 315 with the respective bronchus balloons 320 and 321 touch the carina 5, resulting in the balloons 320, 321 and thus the support parts 314 and 315 being pushed apart when the respiration tube 301 is being inserted further (FIG. 14).

Thereafter, the bronchus balloons 320 and 321 can be deflated and the respiration tube 301 is supported on the carina 5 by means of the support 313 (FIG. 15). Depending on which half of the lungs is to be given artificial respiration, either bronchus balloon 321 (FIG. 16) or bronchus balloon 320 (FIG. 17) can then be inflated completely. This makes it possible to selectively apply artificial respiration to both halves of the lungs, so that the other half of the lungs can be operated on.

An artificial respiration system according to the invention, for example one of the two embodiments as shown in FIGS. 1-11, may furthermore be provided with a compensating device. The compensating device connects the bronchus blocker to the respiration tube. In this case, the compensating device exerts a force in the longitudinal direction of the respiration tube and the insertion rod, for example by means of spring means. If the respiration tube then moves with respect to the carina, the compensating device will hold the bronchus blocker with its support against the carina. As an alternative to such a compensating device, a user may also hold the bronchus blocker in place.

FIG. 19 shows a first embodiment of a compensating device for an artificial respiration system 400. The artificial respiration system 400 comprises a swivel connector 404 which is connected to the respiration tube (not shown). The swivel connector 404 is provided with a diaphragm 405 for receiving a tube-shaped holder 410 in an airtight manner. The tube-shaped holder 410 is suitable for receiving, for example, a second and optionally third insertion tube (not shown), which have a support near their far end, as has been described above with respect to the first embodiment. The tube-shaped holder 410 itself may also have a support near its far end, as has been described above with respect to the second embodiment.

The compensating device 430 comprises a connecting ring 431, spring means in the shape of elastic bands 432 and a clamp 433. The connecting ring 431 connects the elastic bands 432 to the tube-shaped holder 410. The clamp 433 connects the elastic bands 432 to the swivel connector 404.

In use, first the tube-shaped holder 410 and any insertion tubes will be inserted in such a manner that the support (not shown) is supported on the carina, as has been described above in detail. Subsequently, the tube-shaped holder 410 is connected to the swivel connector 404 by means of the compensating device 430. In this case, the clamp 433 and/or connecting ring 431 are positioned alongside the swivel connector 404 and/or the tube-shaped holder 310 in the axial direction in such a manner that the elastic bands 432 exert sufficient pressure force on the tube-shaped holder 410. This pressure force is directed axially and of such magnitude that the support (not shown) is supported on the carina under slight pressure. The spring coefficient of the elastic bands 432 is so low that the tube-shaped holder 410 and the swivel connector 404 are able to move relative to one another to a sufficient degree without the pressure force becoming zero or the load on the support of the carina becoming too great. A sufficient degree of movement is considered to be the difference in the distance traveled by the respiration tube between the position of the head of a patient tilted in a forward direction and the position of the head tilted in a backward direction.

Figure 20:
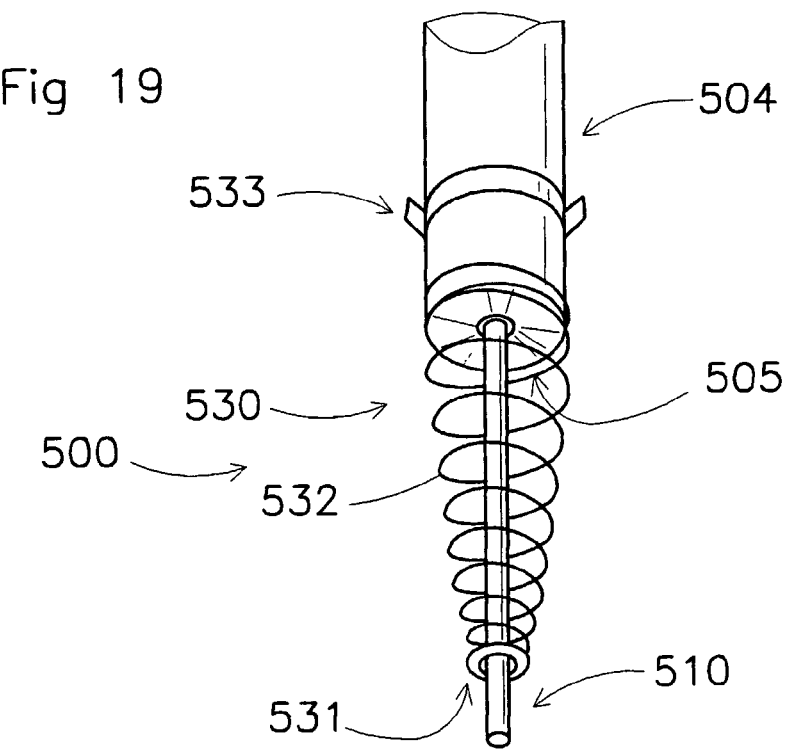
FIG. 20 shows a second embodiment of a compensating device.

FIG. 20 shows a second embodiment of a compensating device for an artificial respiration system 500. The artificial respiration system 500 comprises a swivel connector 504 which is connected to a respiration tube (not shown). The swivel connector 504 is provided with a diaphragm 505 for receiving a tube-shaped holder 510 in an airtight manner. The tube-shaped holder 510 forms part of a bronchus blocker, which has not been shown in any more detail in this figure, but may be similar to one of the above-described embodiments.

The compensating device 530 comprises a connecting ring 531, spring means in the form of a coil spring 532 and a clamp 533. The connecting ring 531 connects the coil spring 532 with the tube-shaped holder 510. The clamp 533 connects the coil spring 532 to the swivel connector 504.

The compensating device 530 can be used in a similar way to the compensating device 430 from FIG. 19.

Many variants are possible in addition to the embodiments shown. Thus, it is possible to provide two support parts, each with a bronchus balloon, on one insertion rod. Such an insertion rod with double support parts and bronchus balloons may be used in combination with an insertion rod with a single support part, as shown with reference to FIGS. 1-5. When the insertion rods have been inserted as far as the carina, in a manner similar to that described with reference to these figures, the insertion rod with the double support parts can be pushed further into the respective main bronchus and the bronchus balloons on this insertion rod are both partly inflated. Thereafter, the respective bronchus balloons can be pushed into the sub-bronchi in order thus to be able to seal off individual lung lobes. The respective insertion rod will then be supported by its support parts on the branching of the respective sub-bronchi.

The insertion rods do not have to be flexible over their entire length, but may be substantially stiff, with the exception of the pivot points where the respective insertion rod joins a support part.

A hollow insertion rod is preferred as it is also possible to inflate a bronchus balloon through the respective lumen. A solid insertion rod is likewise possible, for example if no bronchus balloons are used as blocking means, or if the respective balloon is inflated in another way. However, it is also possible to provide the insertion rods with a plurality of, for example two, separate lumens. The first lumen is then used for inflating or deflating a bronchus balloon. The second lumen extends completely through the respective support part and thus also through the respective bronchus balloon, which makes it possible to use it in order to be able to deflate the respective sealed half of the lungs.

Alternatives to the balloons shown may be used as blocking means, such as a plug, or materials or means which can be enlarged or expanded by means other than inflating, for example by the action of heat, moisture or other (environmental) conditions.

A blocking means may be provided on the end of the respective insertion rod, but the insertion rod may also extend beyond the blocking means for a certain distance.

In this manner, the invention provides a bronchus blocker and an artificial respiration system with which the halves or lobes of lungs may be sealed off as desired, so that artificial respiration may be applied to those parts of the lungs which have not been sealed off. To this end, it is not necessary to insert a respiration tube into the bronchi to which artificial respiration is to be applied. The bronchus blocker according to the invention remains in its desired position very well, due to a support which is supported on the carina or a branching of the sub-bronchi. In this case, a slight pressure may be exerted on the bronchus blocker so as to keep the bronchus blocker in its position in a secure manner. No endoscope is required to fit the bronchus blocker.

What is claimed is:

1. An artificial respiration system comprising:
a bronchus blocker for sealing off one bronchus of two bronchi, the bronchus blocker including an insertion rod and a blocking means, the blocking means being provided near one end of the insertion rod in order to be inserted by means thereof into the one bronchus, the bronchus blocker further including a support for supporting the bronchus blocker on a bronchial branching, the support of the bronchus blocker includes two support parts each intended for support on either side of the bronchial branching, each of the two support parts being expandable, wherein the bronchus blocker is configured to completely seal the one bronchus; and
a respiration tube, the respiration tube consisting of one tube, the respiration tube including at least one first lumen, in which the respiration tube is suitable for receiving the bronchus blocker in order to insert the bronchus blocker into a trachea, wherein the respiration tube is configured to remain within the trachea without extending into the brachial branching and provide air to the other bronchus.

2. The artificial respiration system of claim 1, wherein the support of the bronchus blocker is fitted on the insertion rod so as to be movable, in order to occupy either a supporting position or an insertion position.

3. The artificial respiration system of claim 2, wherein the support of the bronchus blocker is rotatable with respect to the insertion rod.

4. The artificial respiration system of claim 2, wherein the support of the bronchus blocker can be displaced laterally with respect to the insertion rod.

5. The artificial respiration system of claim 1, wherein each of the two expandable support parts is a balloon which is inflatable via a lumen in the insertion rod.

6. The artificial respiration system of claim 1, wherein the two support parts may be at a support angle (β) with respect to one another.

7. The artificial respiration system according to claim 1, further comprising a compensating device which connects the bronchus blocker and the respiration tube with one another so that they are movable in the longitudinal direction in such a manner that in use the respiration tube is movable with respect to the bronchial branching while the bronchus blocker is supported against the bronchial branching.

8. The artificial respiration system according to claim 7, in which the compensating device comprises a spring means.

9. The artificial respiration system according to claim 1, in which the respiration tube functions as the insertion rod.

10. The artificial respiration system according to claim 1, in which the respiration tube is provided with an expandable sealing means around its circumference in order to connect the exterior of the tube with the trachea in an airtight manner.

11. The artificial respiration system according to claim 1, in which the respiration tube comprises at least one second lumen.

12. A method of using a bronchus blocker according to claim 1, comprising:
 inserting the respiration tube into the trachea; and
 inserting the bronchus blocker into the one bronchus, wherein the bronchus blocker seals off the one bronchus of a respiratory system.

* * * * *